(12) United States Patent
Hofer Kraner et al.

(10) Patent No.: US 10,429,680 B2
(45) Date of Patent: Oct. 1, 2019

(54) OPTICAL GLARE PROTECTION FILTER

(71) Applicant: Optrel Holding AG, Appenzell (CH)

(72) Inventors: Ramon Hofer Kraner, Herisau (CH); Martin Esposito, Rapperswil (CH); Jonathan Heusser, Uerikon (CH); Yang Sheng, Wattwil (CH); Marco Landolt, Näfels (CH); Daniel Bloechinger, Gallenkappel (CH)

(73) Assignee: Optrel Holding AG, Appenzell (CH)

( * ) Notice: Subject to any disclaimer, the term of this patent is extended or adjusted under 35 U.S.C. 154(b) by 0 days.

(21) Appl. No.: 15/825,805

(22) Filed: Nov. 29, 2017

(65) Prior Publication Data

US 2018/0149895 A1    May 31, 2018

(30) Foreign Application Priority Data

Nov. 30, 2016  (EP) ..................................... 16201503

(51) Int. Cl.
*G02F 1/133* (2006.01)
*A61F 9/06* (2006.01)
*G02B 7/00* (2006.01)

(52) U.S. Cl.
CPC ............ *G02F 1/13306* (2013.01); *A61F 9/06* (2013.01); *A61F 9/067* (2013.01); *G02B 7/006* (2013.01)

(58) Field of Classification Search
None
See application file for complete search history.

(56) References Cited

U.S. PATENT DOCUMENTS

| 2006/0285330 | A1 | 12/2006 | Sundell |
| 2008/0165301 | A1* | 7/2008 | Chang ................. G02F 1/13452 349/40 |
| 2014/0168546 | A1* | 6/2014 | Magnusson ........ A41D 13/1184 349/14 |
| 2014/0215673 | A1 | 8/2014 | Lilenthal |
| 2015/0033430 | A1 | 2/2015 | Hofer Kraner et al. |

FOREIGN PATENT DOCUMENTS

EP    2 839 817 A1    2/2015

OTHER PUBLICATIONS

Search Report dated Jun. 7, 2017 issued in corresponding EP patent application No. 16201503.6 (and partial English translation).

* cited by examiner

*Primary Examiner* — Phu Vu
(74) *Attorney, Agent, or Firm* — Posz Law Group, PLC

(57) ABSTRACT

An optical glare protection filter for a glare protection device includes at least one liquid-crystal cell with at least one liquid-crystal layer and at least one first electrode layer for orienting crystal molecules of the at least one liquid-crystal layer, and with at least one first contact element for electrically contacting the at least one first electrode layer. The optical glare protection filter may also include at least one second contact element for electrically contacting the at least one first electrode layer, which is substantially spaced apart from the first contact element.

11 Claims, 7 Drawing Sheets

OPTICAL GLARE PROTECTION FILTER

CROSS REFERENCE TO RELATED APPLICATION

Figure 1:
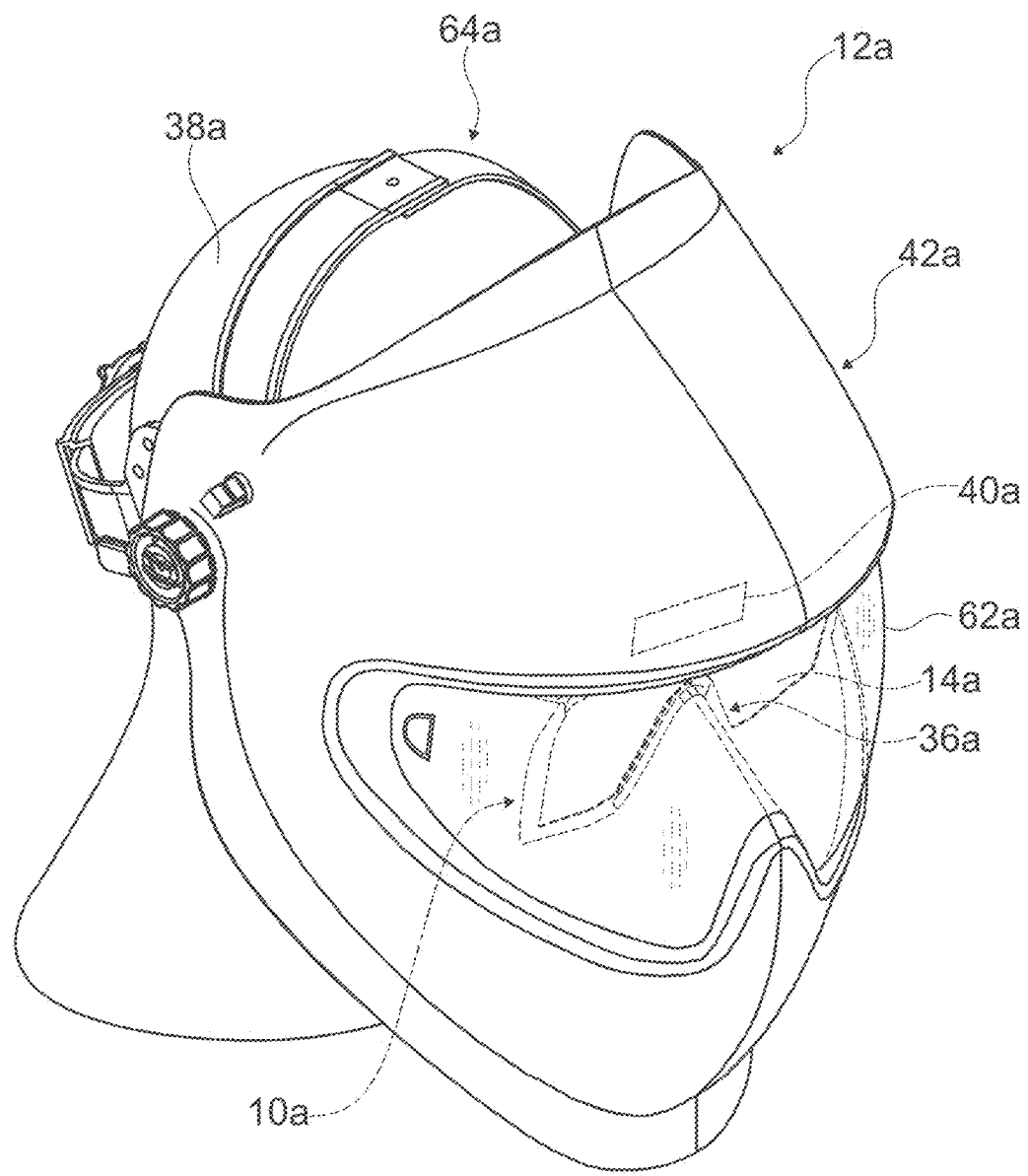

This application is based on and incorporates herein by reference European Patent Application No. 16201503.6 filed on Nov. 30, 2016.

STATE OF THE ART

The invention relates to an optical glare protection filter.

An optical glare protection filter for a glare protection device, with at least one liquid-crystal cell comprising at least one liquid-crystal layer and at least one first electrode layer unit for orienting crystal molecules of the at least one liquid-crystal layer, and with at least one first contact element for electrically contacting the at least one first electrode layer, has already been proposed.

The objective of the invention is in particular to provide a generic device with improved characteristics regarding a switching speed as well as regarding a homogeneity of a switching speed distribution, The objective is achieved, according to the invention, by the features of patent claim 1 while advantageous implementations and further developments of the invention will become apparent from the subclaims.

Advantages of the Invention

The invention is based on an optical glare protection filter for a glare protection device, with at least one liquid-crystal cell comprising at least one liquid-crystal layer and at least one first electrode layer unit for orienting crystal molecules of the at least one liquid-crystal layer, and with at least one first contact element for electrically contacting the at least one first electrode layer.

It is proposed that the optical glare protection filter comprises at least one second contact element for electrically contacting the at least one first electrode layer unit, which is substantially spaced apart from the first contact element. Preferably the liquid-crystal cell comprises at least two electrode layer units, which are together configured for orienting crystal molecules of the at least one liquid-crystal layer. Preferentially the electrode layer units are arranged on opposite sides of the at least one liquid-crystal layer. Preferably the first contact element and the second contact element are arranged on a circumference of the electrode layer unit. Particularly preferably the first contact element and the second contact element have the same potential. Preferentially the first contact element and the second contact element are implemented by the same pole, like in particular a positive pole or a negative pole. By an "optical glare protection filter" is in particular an optical filter for a glare protection device to be understood, which in particular implements a protective glass and/or a synthetic protective glass. It is preferably to mean, in particular, an optical filter the light permeability of which is implemented in such a way that it is adjustable. It is preferentially in particular to mean an optical welding protection filter with an automatic darkening. Especially preferably the glare protection filter comprises at least one liquid-crystal plane which is switchable in the transmittance. A variety of implementations of the optical glare protection filter are conceivable which are deemed expedient by someone skilled in the art, and an optical glare protection filter is in particular to mean an ADP, also named an "automatic darkening filter" or an "automatic welder's protection filter". By a "glare protection device" is in particular, in this context, a device to be understood which is configured for protecting a user from excess brightness and/or sparks. Preferably it is in particular to mean a device serving to protect a user's eyes and/or a user's facial region during a welding and/or grinding process. Preferentially it is in particular to mean a device which in particular serves to protect a user's eyes at least during a welding process. A variety of implementations of a protection device, deemed expedient by someone skilled in the art, are conceivable, e.g. as a welding helmet, a welding screen, a welding mask and/or a welding shield. Furthermore a variety of liquid-crystal cells deemed expedient by someone skilled in the art are conceivable, like in particular a TN liquid-crystal cell featuring the Twisted Nematic technology. Principally, however, other embodiments of the liquid-crystal cells which are deemed expedient by someone skilled in the art are also conceivable, e.g. as STN liquid-crystal cells with the Super-Twisted Nematic technology, as DSTN liquid-crystal cells with the Double Super-Twisted Nematic technology, as TSTN liquid-crystal cells with the Triple Super-Twisted Nematic technology, as VA liquid-crystal cells with the Vertical Alignment technology, in particular PVA/MVA liquid-crystal cells with the Patterned Vertical Alignment technology and/or Multi-Domain Vertical Alignment technology, as IPS liquid-crystal cells with the In-Plane Switching technology, as FLCD liquid-crystal cells, i.e. ferroelectric liquid-crystal cells, and/or as TN liquid-crystal cells with the Guest-Host technology.

An "electrode layer unit" is in particular to mean, in this context, a layer-like unit, preferably a thin layer-like unit, of the liquid-crystal cell which is configured for orienting crystal molecules of the liquid-crystal cell. The electrode layer unit is preferably configured to generate, if a voltage is applied, an electric field that orients the crystal molecules, Preferentially the electric field is generated between two electrode layer units of the liquid-crystal cell, An electrode layer unit may herein consist of one single layer, of a plurality of layers that are arranged above one another and/or of a plurality of partial layer segments which are arranged in a layer plane. Principally, however, further implementations of the electrode layer unit are also conceivable which are deemed expedient by someone skilled in the art. The electrode layer unit is in particular implemented by an electrode that is embodied as a layer. Preferably each electrode layer unit implements a potential. The liquid-crystal cell in particular comprises two electrode layer units having different potentials and thus implementing different electrodes. Moreover, by a "contact element" is in particular, in this context, an element to be understood which is configured for electrically contacting an electrode layer unit. Preferably it is in particular to be understood as an element implementing a contacting point of the electrode layer unit which electrically contacts the electrode layer unit through a sealing of the liquid-crystal cell. It is preferably in particular to be understood as an element which directly contacts the electrode layer unit and via which a voltage may be applied to the electrode layer unit. The contact element may herein be embodied of a single contacting point or of a contacting plane. The contact element is in particular implemented by an electrical contact. "Substantially spaced apart" is in particular to mean, in this context, that a minimum distance between the contact elements, in particular between the contacting points of the contact elements with regard to the electrode layer, amounts to at least 1 cm, preferably at least 2 cm and particularly preferably at least 3 cm. It is preferentially in particular to mean that a minimum distance, in particular along the circumference of the electrode layer, between the contact elements, in particular between the contacting points of the contact elements for contacting the electrode layer, amounts to at least 1%, preferably at least 3%, preferentially at least 5% and especially preferentially at least 10% of a total circumference of the electrode layer unit along an outer contour. The total circumference of the electrode layer unit preferably extends in a main extension plane of the electrode layer unit and in particular embodies a maximum circumference of the electrode layer. Herein a "main extension plane" of a layer and/or of a structural unit is in particular to mean a plane which is parallel to a largest side surface of a smallest imaginary rectangular cuboid just still entirely enclosing the layer and/or the structural unit, the plane in particular extending through the center point of the rectangular cuboid. "Configured" is in particular to mean specifically programmed, designed and/or equipped. By an object being configured for a certain function is in particular to be understood that the object fulfills and/or implements said certain function in at least one application state and/or operating state.

The implementation according to the invention in particular allows providing an advantageous glare protection filter. In particular, an advantageous fast and homogeneous response behavior of the glare protection filter may be rendered available. By multiple contacting of the at least one first electrode layer unit an advantageously great switching speed of the liquid-crystal cell is achievable. Furthermore an advantageously homogeneous switching speed distribution of the liquid-crystal cell is achievable.

It is also proposed that the at least one second contact element is arranged on a side of the first electrode layer unit that is situated opposite the at least one first contact element. Preferably at least a partial region of the first electrode layer unit is arranged between the first contact element and the second contact element. Preferentially the first contact element and the second contact element are arranged in opposite points of a total circumference of the electrode layer unit. This in particular allows providing an especially advantageous glare protection filter. Moreover an advantageously homogeneous switching speed distribution of the liquid-crystal cell is achievable. Due to the multiple contacting, advantageously even charging may be rendered possible. Charging of the liquid-crystal cell from different directions is achievable, as a result of which the liquid-crystal cell may be charged in an advantageously homogeneous as well as quick fashion. Darkening is achievable within a very short time period, in particular approximately 100 µs. The advantageous switching speed distribution is in particular also relevant for a measurement of the switching time as, in accordance with standard requirements (EN379), there is no requirement regarding a measuring location. That means a location may be determined by an examiner, who may then examine an unfavorable location. With multiple contacting the impact of the measuring location is reduced.

Further it is proposed that, for electrically contacting the at least one first electrode layer, the optical glare protection filter comprises at least one further contact element which is substantially spaced apart from the first contact element and the second contact element.

A contacting point of the further contact element for contacting the electrode layer unit is preferably substantially spaced apart from the contacting points of the first contact element and the second contact element for contacting the electrode layer unit. Preferably a distance of the first contact element to the second contact element is at least substantially equivalent to a distance between the second contact element and the further contact element. This in particular allows providing an especially advantageous glare protection filter. Preferentially the multiple contacting allows advantageously even charging. By way of the great number of contacts an advantageous charging characteristic is achievable. Charging of the electrodes and the liquid-crystal layer—and thus of the entire liquid-crystal cell acting as a capacitor—may be effected advantageously fast due to the multiple contacting. When comparing global darkening, which approximately corresponds to full charging, at one point in time t, an increase of total darkening with the number of contacts may be observed. An increase of the darkening speed and/or of the charging speed may be in a range from 0.5% to 50%.

Beyond this it is proposed that, for the purpose of electrically contacting the at least one first electrode layer unit, the contact elements are distributed substantially evenly in a circumferential direction around the first electrode layer unit. Preferably, for electrically contacting the at least one first electrode layer unit, the contact elements are distributed at least substantially evenly in a circumferential direction around the first electrode layer unit, along a circumference of the first electrode layer unit. "Distributed at least substantially evenly in a circumferential direction around the first electrode layer unit" is in particular to mean, in this context, that the distances along the circumference of the electrode layer unit between two contact elements which are adjacent along the circumference of the electrode layer unit are at least substantially identical. It is preferentially in particular to mean that a smallest distance between two contact elements which are adjacent along the circumference of the electrode layer unit amounts to at least 20%, preferably at least 40% and particularly preferably at least 60% of a greatest distance, along the circumference of the electrode layer unit, between two contact elements which are adjacent along the circumference of the electrode layer unit. This allows achieving an advantageously homogeneous switching speed distribution of the liquid-crystal cell. By the multiple contacting an advantageously even charging may be rendered feasible. Charging of the liquid-crystal cell from different directions is achievable, allowing the liquid-crystal cell to be charged in an advantageously homogeneous as well as advantageously quick fashion.

It is further proposed that the optical glare protection filter comprises a nose cut-out, which is configured to at least partly accommodate a user's nose. By a "nose cut-out" is in particular to be understood, in this context, an immaterial recess in an at least partly translucent partial region of the optical glare-protection filter, which is in at least one operating position of the glare protection device at least partly configured to at least partly accommodate a user's nose. Preferably the recess is in each point of at least one plane, which is in particular parallel to a main extension plane of the glare protection filter, in an angle range of at least 180 degrees, encompassed by a material partial region, in particular in an at least partly translucent partial region of the optical glare protection filter. Preferentially the optical glare protection filter extends around a user's nose in at least one operating position of the protection device. Especially preferentially a vertical extension of the nose cut-out is at least 10%, preferably at least 30%, preferentially at least 50% and particularly preferably at least 55% of a vertical extension of the optical glare protection filter. This in particular allows achieving an advantageously high comfort level of the optical glare protection filter. Due to the multiple contacting, an advantageously homogeneous switching speed distribution and a quick darkening of the liquid-crystal cell are achievable.

Furthermore it is proposed that the optical glare protection filter comprises at least two further contact elements, respectively electrically contacting a second electrode layer unit of the at least one liquid-crystal cell. Preferably the liquid-crystal cell comprises a second electrode layer unit which extends in parallel to the first electrode layer unit. The second electrode layer unit is preferably arranged on a side of the liquid-crystal layer that is situated opposite the first electrode layer unit. Preferentially the second electrode layer unit is connected to contact elements which correspond to the contact elements which electrically contact the first electrode layer unit. The contact elements which electrically contact the second electrode layer unit are also arranged substantially spaced apart from one another. The contact elements which electrically contact the second electrode layer unit have, with respect to the second electrode layer unit, the same arrangement as the contact elements which electrically contact the first electrode layer unit have with respect to the first electrode layer. This allows making an advantageous glare protection filter available. In particular, an advantageously quick and homogeneous response behavior of the glare protection filter may be provided. By multiple contacting of the at least one first electrode layer unit it is possible to achieve an advantageously high switching speed of the liquid-crystal cell. Moreover an advantageously homogeneous switching speed distribution of the liquid-crystal cell is achievable.

The arrangement of the contact elements which electrically contact the second electrode layer unit may be embodied congruently to or differently from the arrangement of the contact elements which electrically contact the first electrode layer unit.

Furthermore a glare protection device with the at least one optical glare protection filter and with at least one control and/or regulation unit is proposed, which is configured to control and/or regulate a permeability of the optical glare protection filter depending on a captured operative state and/or on a light irradiation. By a "control and/or regulation unit" is in particular, in this context, a unit with at least one control electronics component is to be understood. A "control electronics component" is in particular to mean a unit with at least one electronic circuit, which is preferably composed of voltage components and reference control components. Principally, however, the control electronics component may also have a more complex structure, like in particular using an application-specific integrated circuit (ASIC) and/or a micro-controller component. This in particular allows rendering an advantageous glare protection device available. In particular, a glare protection device may be rendered available with an optical glare protection filter charging in an advantageously quick and homogeneous manner.

It is also proposed that the at least one control and/or regulation unit actuates the optical glare protection filter at least substantially simultaneously via the at least one first contact element and the one second contact element. Preferably the optical glare protection filter is actuated, by means of the control and/or regulation unit, simultaneously via all contact elements. As a result of this, advantageously fast charging of the optical glare protection filter is achievable. Principally it would however also be conceivable that the control and/or regulation unit actuates the contact elements, for example, depending on a direction of an irradiation incidence. It would, for example, be conceivable that, in case of an irradiation incidence from a side, the optical glare protection filter darkens the optical glare protection filter starting from said side.

Moreover it is proposed that the glare protection device comprises at least one shield unit, in which the at least one optical glare protection filter is fixedly accommodated. By a "shield unit" is in particular, in this context, a unit to be understood which is in a regular operating position arranged in front of a user's face. Preferably it is in particular to be understood as a unit which, in an operative position of the glare protection device, covers at least a substantial portion of a user's face. It is preferentially in particular to be understood as a unit configured to protect a face, e.g. from flying sparks. Preferably the shield unit is in particular configured to implement a protective barrier between a work space and a user's face. This allows rendering an advantageous glare protection device available. An advantageously safe glare protection device may be rendered available.

The optical glare protection filter according to the invention and the glare protection device are herein not to be limited to the application and implementation form described above. In particular, the optical glare protection filter according to the invention as well as the glare protection device may, for fulfilling a functionality herein described, comprise a number of respective elements, structural components and units that differs from a number that is mentioned here.

DRAWINGS

Further advantages may be gathered from the following description of the drawings. In the drawings five exemplary embodiments of the invention are shown. The drawings, the description and the claims contain a plurality of features in combination. Someone skilled in the art will purposefully also consider the features separately and will find further expedient combinations.

Figure 2:
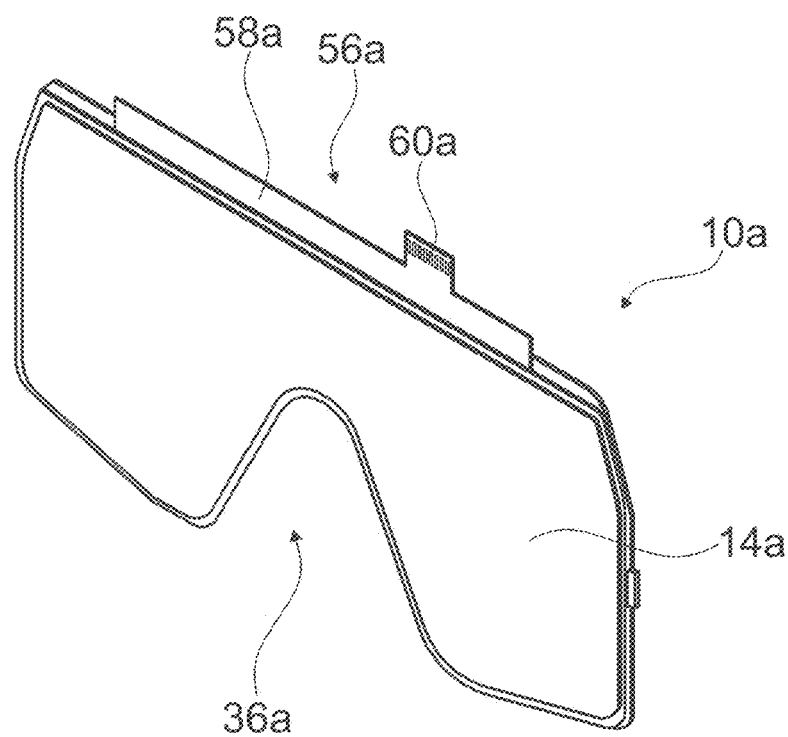
Figure 3:
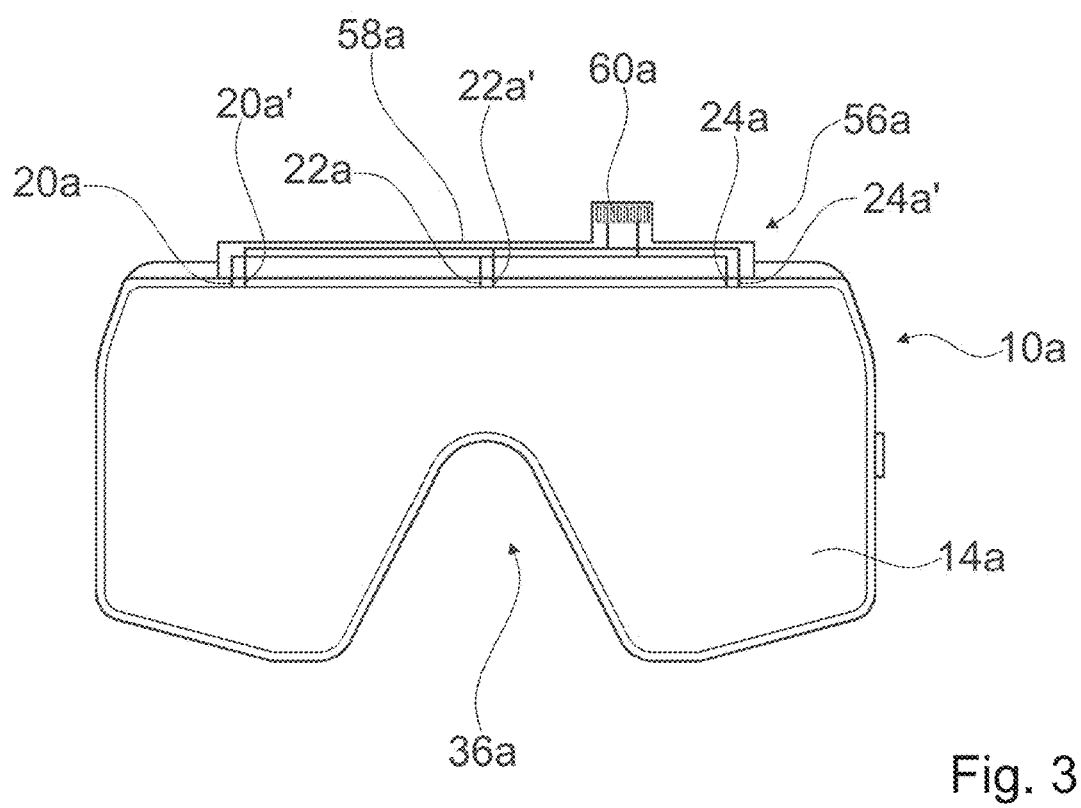
Figure 4:
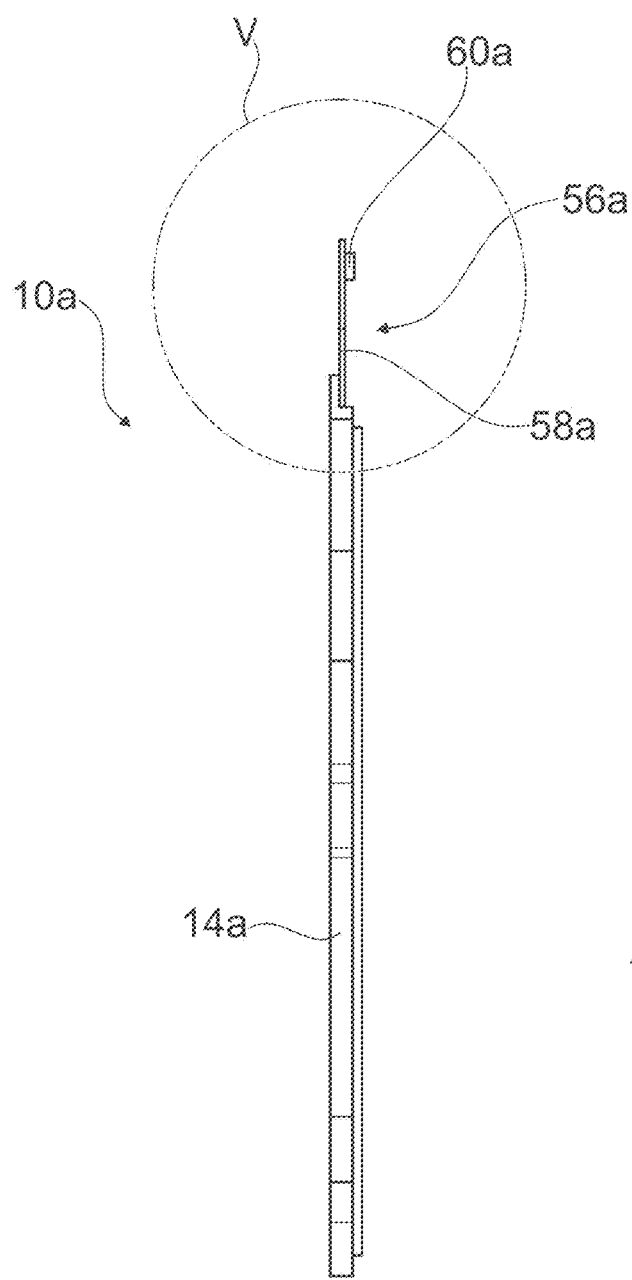
Figure 5:
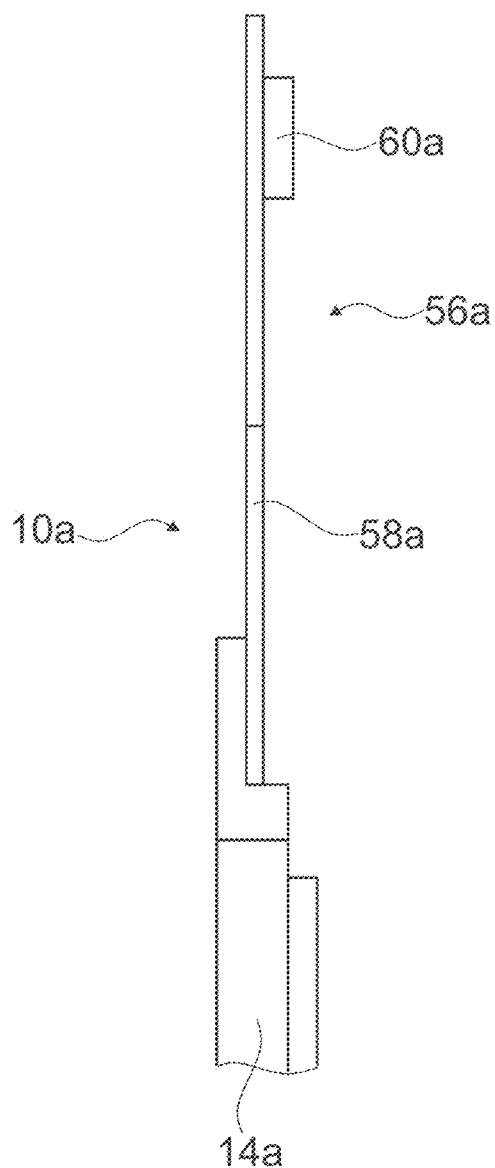
Figure 6:
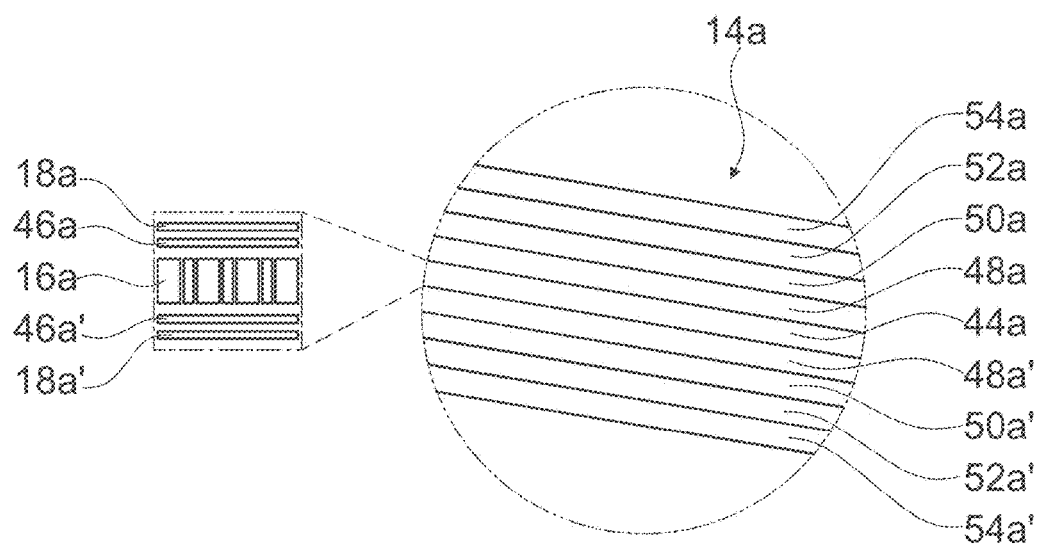
Figure 7:
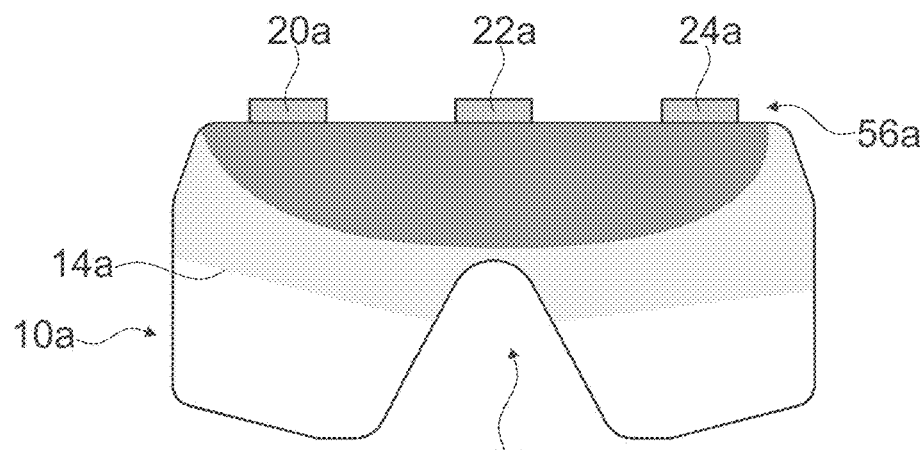
Figure 8:
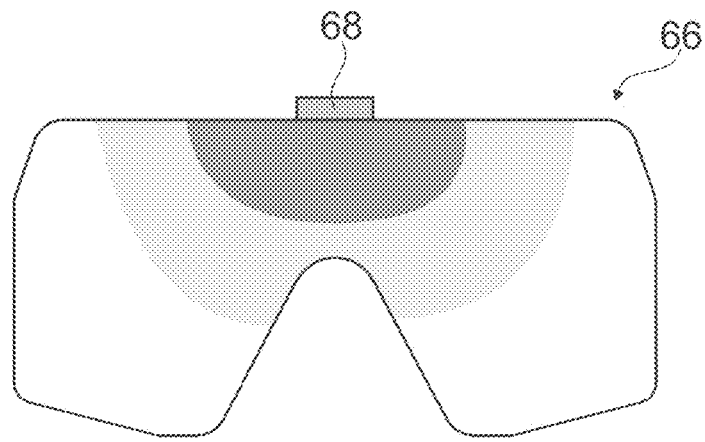
Figure 9:
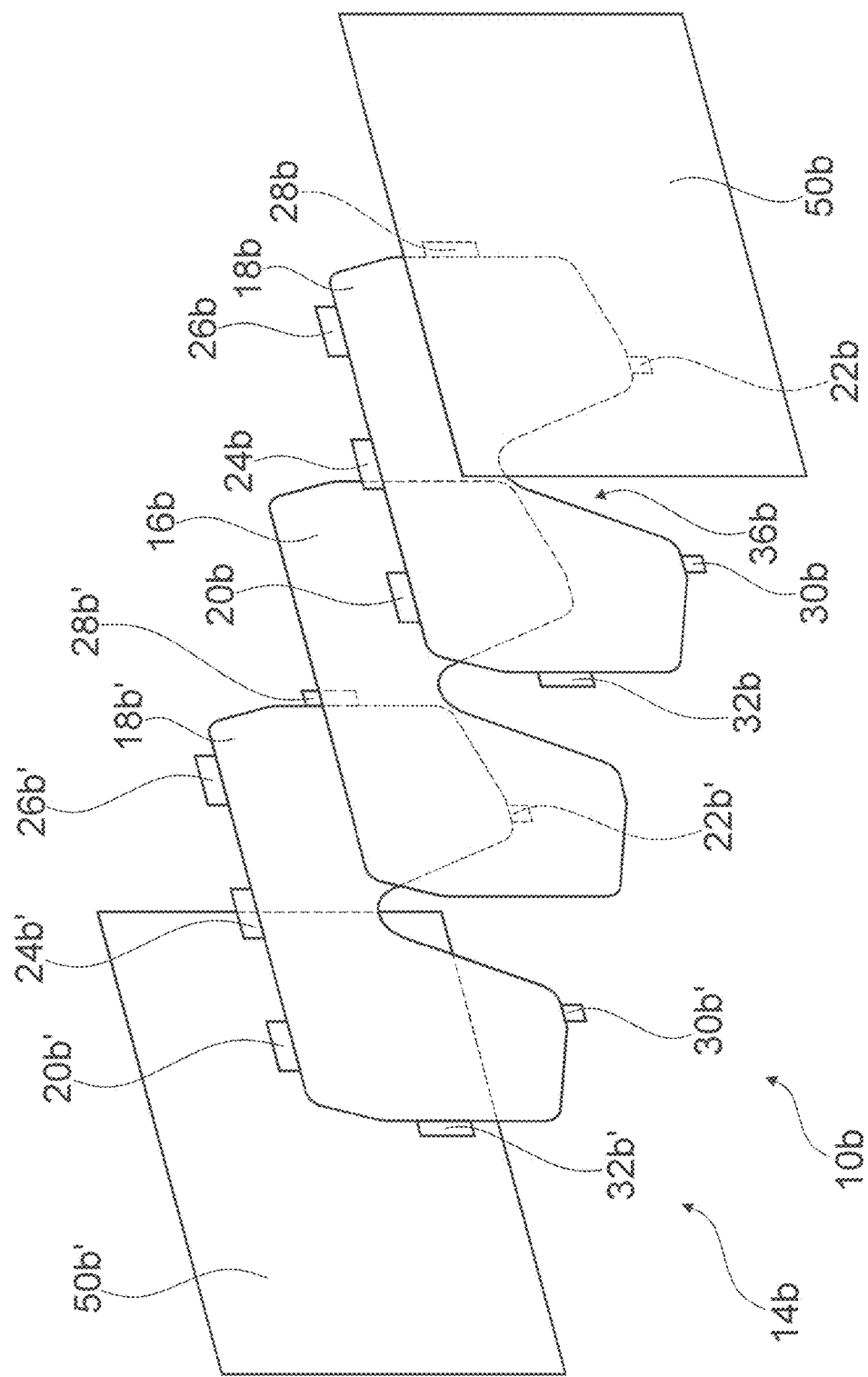
Figure 10:
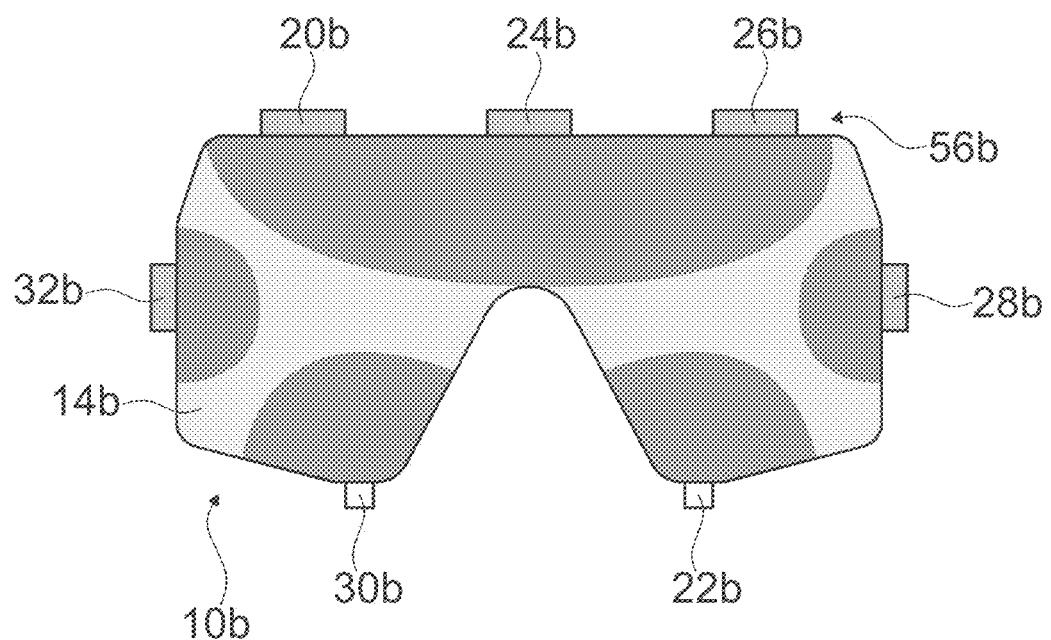
Figure 11:
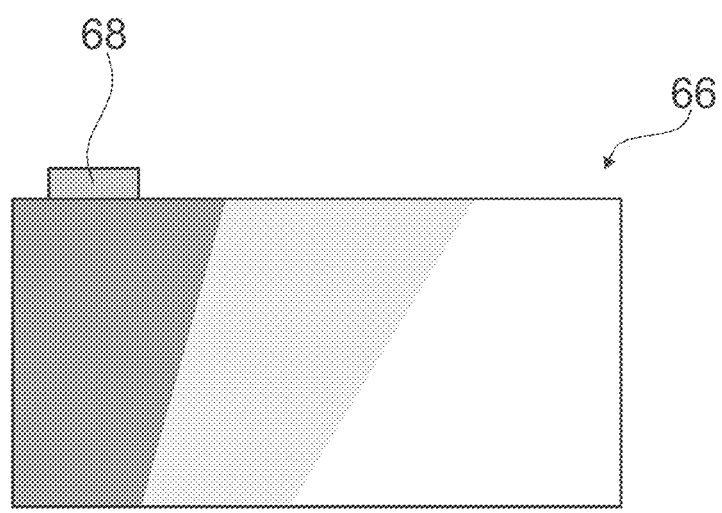
Figure 12:
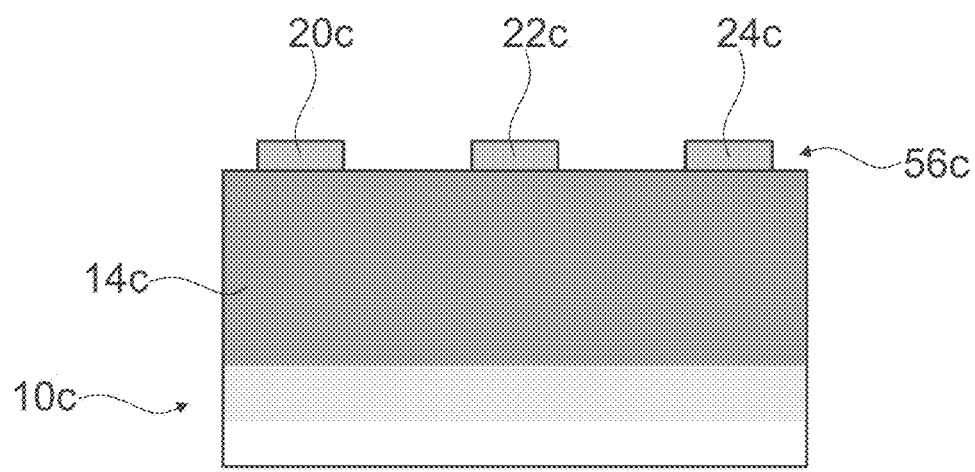
Figure 13:
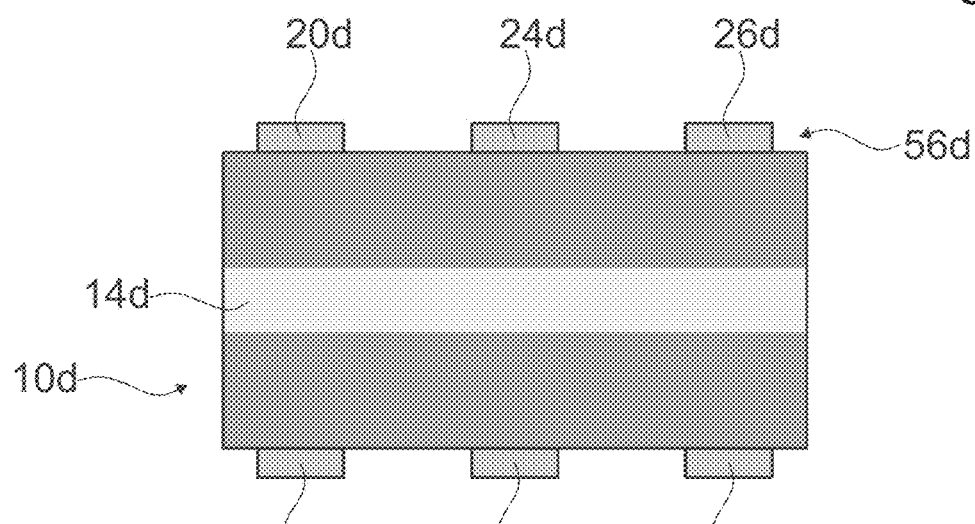
Figure 14:
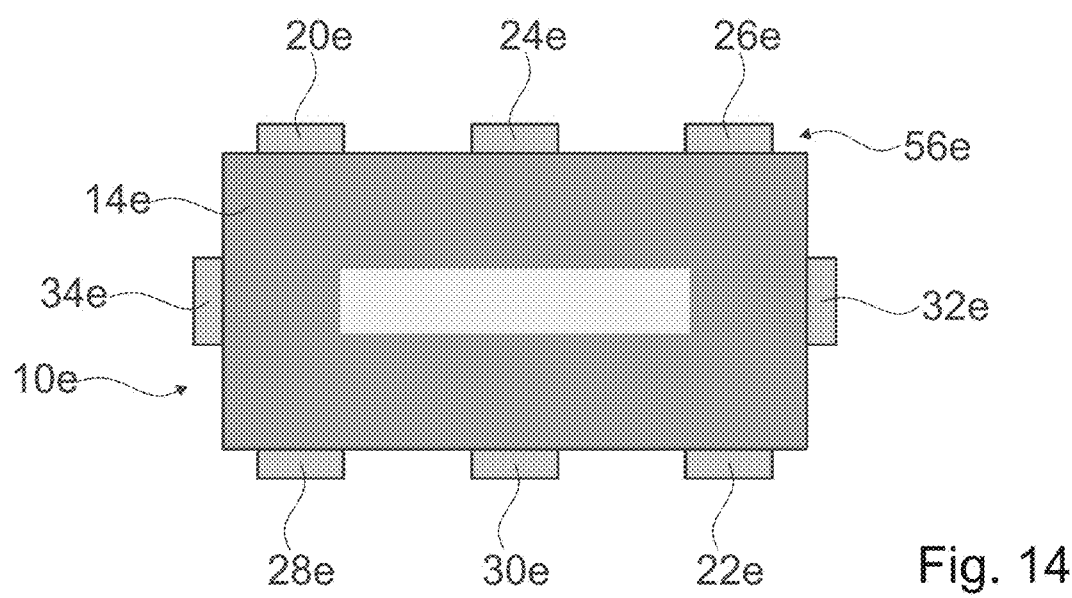

It is shown in:

FIG. 1 a glare protection device with a shield unit, with an optical glare protection filter according to the invention and with a front cover plate on a user's head, in a schematic presentation, FIG. 2 the optical glare protection filter according to the invention, with a liquid-crystal cell and with a contact unit, in a schematic presentation, FIG. 3 the optical glare protection filter according to the invention with the liquid-crystal cell and with the contact unit, which comprises a plurality of contact elements, in a schematic front view, FIG. 4 the optical glare protection filter according to the invention with the liquid-crystal cell and with the contact unit, in a schematic side view, FIG. 5 a partial section V of the optical glare protection filter according to the invention with the liquid-crystal cell and with the contact unit, in a schematic side view, FIG. 6 a partial section VI of the liquid-crystal cell of the optical glare protection filter according to the invention, in a schematic sectional view, FIG. 7 the optical glare protection filter according to the invention during a darkening process at a point in time t, in a schematic front view, FIG. 8 an optical glare protection filter with only one contact element during a darkening process at a point in time t, in a schematic front view, FIG. 9 an alternative optical glare protection filter according to the invention with a liquid-crystal cell and with a contact unit, in a schematic exploded view, FIG. 10 the alternative optical glare protection filter according to the invention during a darkening process at a point in time t, in a schematic front view, FIG. 11 an optical glare protection filter with only one contact element during a darkening process at a point in time t, in a schematic front view, FIG. 12 another alternative optical glare protection filter according to the invention during a darkening process at a point in time t, in a schematic front view, FIG. 13 a further alternative optical glare protection filter according to the invention during a darkening process at a point in time t, in a schematic front view, and FIG. 14 a further alternative optical glare protection filter according to the invention during a darkening process at a point in time t, in a schematic front view.

DESCRIPTION OF THE EXEMPLARY EMBODIMENTS

FIG. 1 shows a glare protection device 12a on a head of a user 38a. The glare protection device 12a is configured to be worn by a user 38a on his head during operation. FIG. 1 shows the glare protection device 12a in an operating position. It is implemented by a welding helmet. Principally however a different implementation of the glare protection device 12a, deemed expedient by someone skilled in the art, would also be conceivable.

The glare protection device 12a comprises an optical glare protection filter 10a. The optical glare protection filter 10a is implemented by an electro-optical filter, The optical glare protection filter 10a is embodied by an automatic darkening filter, ADF in short. The optical glare protection filter 10a comprises a liquid-crystal cell 14a. The liquid-crystal cell 14a consists of a plurality of layers. The liquid-crystal cell 14a is embodied as a multi-layer compound. A number of layers is here merely given as an example and may principally vary. The liquid-crystal cell 14a is implemented by a TN liquid-crystal cell, The liquid-crystal cell 14a is thus based on the Twisted Nematic technology. Principally however other implementations of the liquid-crystal cell 14a, deemed expedient by someone skilled in the art, would also be conceivable, e.g. as an STN liquid-crystal cell with the Super-Twisted Nematic technology, as a DSTN liquid-crystal cell with the Double Super-Twisted Nematic technology, as a TSTN liquid-crystal cell with the Triple Super-Twisted Nematic technology, as a VA liquid-crystal cell with the Vertical Alignment technology, in particular PVA/MVA liquid-crystal cell with the Patterned Vertical Alignment technology and/or Multi-Domain Vertical Alignment technology, as an IPS liquid-crystal cell with the In-Plane Switching technology, as an FLCD liquid-crystal cell, i.e. a ferroelectric liquid-crystal cell, and/or as a TN liquid-crystal cell with the Guest-Host technology. The liquid-crystal cell 14a comprises a liquid-crystal layer 16a. The liquid-crystal cell 14a comprises a liquid-crystal plane 44a. The liquid-crystal plane 44a is implemented by a translucent liquid-crystal plane. The liquid-crystal plane 44a comprises the liquid-crystal layer 16a. In the liquid-crystal layer 16a a plurality of crystal molecules as well as spacer elements are located. On both sides of the liquid-crystal layer 16a a respective polyimide layer 46a, 46a' is arranged, Principally however a different layer for orienting the molecules that is deemed expedient by someone skilled in the art would also be conceivable. The liquid-crystal cell 14a further comprises a first electrode layer unit 18a for orienting crystal molecules of the liquid-crystal layer 16a. The liquid-crystal cell 14a moreover comprises a second electrode layer unit 18' for orienting crystal molecules of the liquid-crystal layer 16a. The electrode layer units 18, 18' together serve for orienting crystal molecules of the liquid-crystal layer 16a. The electrode layer units 18a, 18a' are respectively arranged on sides of the polyimide layers 46a, 46a' facing away from the liquid-crystal layer 16a. The electrode layer units 18a, 18a' are each embodied by a single layer. Principally it would however also be conceivable that the electrode layer units 18a, 18a' are respectively embodied of a plurality of layers arranged above one another and/or of a plurality of partial layer segments arranged in a layer plane. The electrode layer units 18a, 18a' are each implemented by a transparent iridium tin oxide layer. Principally however a different implementation, deemed expedient by someone skilled in the art, would also be conceivable, e.g. as an aluminum zinc oxide layer or as a layer of a comparable translucent electrically conductive material. Furthermore, on both sides of the liquid-crystal plane 44a of the liquid-crystal cell 14a there is respectively one polarization layer 48a, 48a', The polarization layers 48, 48a' respectively serve for a polarization of incident light. On sides of the polarization layers 48a, 48a' facing away from the liquid-crystal plane 44a, a respective plate 50a, 50a' is arranged. The plates 50a, 50a' are made of a synthetic material or of glass. The plates 50a, 50a' are made of polycarbonate. Optionally a respective anti-reflection layer 52a, 52a' and a hard coating 54a, 54a' are implemented on an outer side of the plates 50a, 50a' (FIG. 6).

The optical glare protection filter 10a furthermore comprises a first contact element 20a. The first contact element 20a is configured for electrically contacting the first electrode layer unit 18a. The optical glare protection filter 10a further comprises a second contact element 22a for electrically contacting the first electrode layer unit 18a. The second contact element 22a is substantially spaced apart from the first contact element 20a. A contacting point of the second contact element 22a for contacting the first electrode layer unit 18a is substantially spaced apart from a contacting point of the first contact element 20a for contacting the first electrode layer unit 18a. The optical glare protection filter 10a also comprises a further contact element 24a. The further contact element 24a is also configured for electrically contacting the first electrode layer unit 18a. The further contact element 24a is substantially spaced apart from the first contact element 20a and from the second contact element 22a. A contacting point of the further contact element 24a for contacting the first electrode layer unit 18a is substantially spaced apart from the contacting points of the first contact element 20a and the second contact element 22a for contacting the first electrode layer unit 18a. A distance of the first contact element 20a to the second contact element 22a is substantially equivalent to a distance of the second contact element 22a to the further contact element 24a. The contact elements 20a, 22a, 24a are arranged side by side. The contact elements 20a, 22a, 24a are each arranged on a circumference of the first electrode layer unit 18a. In the positions of the contact elements 20a, 22a, 24a, the first electrode layer unit 18a extends through a sealing (not shown) of the liquid-crystal cell 14a to the outside, where the contact elements 20a, 22a, 24a contact the electrode layer unit 18a with a flexprint. The contact elements 20a, 22a, 24a respectively implement a contacting of the first electrode layer unit 18a. The optical glare protection filter 10a further comprises a contact unit 56a. The contact unit 56a comprises the contact elements 20a, 22a, 24a. The contact elements 20a, 22a, 24a are mounted on a shared flexible circuit board 58a of the contact unit 56a.

The contact unit 56a furthermore implements a contact plug 60a. Via the contact plug 60a the optical glare protection filter 10a is electrically connectable to a control and regulation unit 40a of the glare protection device 12a. Principally however an electrical connection may also be effected, for example, via a soldering surface. The optical glare protection filter 10a moreover comprises three further contact elements 20a', 22a', 24a' respectively electrically contacting the second electrode layer unit 18a' of the liquid-crystal cell 14a. The second electrode layer unit 18a' is connected to contact elements 20a', 22a', 24a', which correspond to the contact elements 20a, 22a, 24a electrically contacting the first electrode layer unit 18a. The contact elements 20a', 22a', 24a' electrically contacting the second electrode layer unit 18a' are respectively substantially spaced apart from one another. The contact elements 20a', 22a', 24a' electrically contacting the second electrode layer unit 18a' have the same arrangement with respect to the second electrode layer unit 18a' as the contact elements 20a, 22a, 24a electrically contacting the first electrode layer unit 18a have with respect to the first electrode layer unit 18a. The contact unit 56a comprises the contact elements 20a', 22a', 24a'. The contact elements 20a', 22a', 24a' are arranged on a side of the flexible circuit board 58a of the contact unit 56a which faces away from the contact elements 20a, 22a, 24a (FIGS. 2 and 3).

However, it would principally also be conceivable that each of the contact elements 20a, 20a', 22a, 22a', 24a, 24a' is individually connected to an actuation point on the electrode layer units 18a, 18a', for example by a wire connection.

Furthermore, the optical glare protection filter 10a comprises a nose cut-out 36a. The nose cut-out 36a is implemented by an immaterial recess in a material portion of the optical glare protection filter 10a. The nose cut-out 36a is implemented by an immaterial recess in a material, partly translucent partial region of the optical glare protection filter 10a. The nose cut-out 36a is configured for partly accommodating a nose of a user 38a. In an operative position of the glare protection device 12a, the nose cut-out 36a is configured to partly accommodate a nose of a user 38a. In an operative position, the optical glare protection filter 10a extends, in a region of the nose cut-out 36a, partly around the nose of the user 38a. The optical glare protection filter 10a has a substantially rectangular basic shape, the nose cut-out 36a extending into the rectangular basic shape. The nose cut-out 36a has a substantially triangular shape. The two sides delimited by the material portion of the optical glare protection filter 10a include an angle of approximately 54°. The nose cut-out 36a extends from a lower edge, in particular from a center of the lower edge, of the glare protection filter 10a towards a geometric center of the optical glare protection filter 10a. The nose cut-out 36a is downwards not delimited by the glare protection filter 10a. A shape of the nose cut-out 36a is adapted to a shape of a nose. A vertical extension of the nose cut-out 36a is at least 45%, preferably at least 50% and especially preferentially at least 55% of a vertical extension of the glare protection filter 10a. The vertical extension of the nose cut-out 36a is approximately 57% of a vertical extension of the glare protection filter 10a.

The glare protection device 12a further comprises the control and regulation unit 40a. The control and regulation unit 40a is configured to control a permeability of the optical glare protection filter 10a depending on a captured operating state and on a light irradiation. The control and regulation unit 40a is for this purpose connected to a sensor unit (not shown in detail). The sensor unit comprises a sensor which is configured to detect a welding process or an occurrence of a bright light which could damage or otherwise affect the eyes of a user 38a. The sensor of the sensor unit is implemented by a photocell. Principally however a different implementation of the sensor of the sensor unit, deemed expedient by someone skilled in the art, would also be conceivable. Furthermore the control and regulation unit 40a is connected to the optical glare protection filter 10a in a manner that is not shown in detail. The control and regulation unit 40a is connected to the optical glare protection filter 10a, in a manner that is not shown in detail, via the contact plug 60a of the contact unit 56a. The control and regulation unit 40a actuates the optical glare protection filter 10a substantially simultaneously via the one first contact element 20a and the one second contact element 22a. The control and regulation unit 40a actuates the optical glare protection filter 10a substantially simultaneously via the contact elements 20a, 20a', 22a, 22a', 24a, 24a'. As a result of this, the liquid-crystal layer 16a of the optical glare protection filter 10a is activated advantageously homogeneously by the control and regulation unit 40a when a welding process or a flash of light is captured via the sensor unit. The liquid-crystal layer 16a of the optical glare protection filter 10a is darkened by the control and regulation unit 40a when a welding process or a flash of light is captured via the sensor unit. The liquid-crystal layer 16a of the optical glare protection filter 10a reduces the permeability for visible light by means of the optical glare protection filter 10a.

The glare protection device 12a also comprises a shield unit 42a. The optical glare protection filter 10a is fixedly accommodated in the shield unit 42a. The optical glare protection filter 10a is accommodated in the shield unit 42a in a fixed position. The glare protection filter 10a is fittingly inserted in a recess in the shield unit 42a. The shield unit 42a is made of a substantially deformation-resistant material. The shield unit 42a is made of a synthetic material which is in particular resistant against sparks and/or other impacts occurring with welding. The shield unit 42a is configured to cover and protect a face and/or head of a user 38a, in particular in accordance with the relevant standards for welding masks. The shield unit 42a has a shape that is partially adapted to a head's shape. In a state when the glare protection device 12a is worn, the shield unit 42a is partially bent around a face of the user 38a (FIG. 1).

The glare protection device 12a further comprises a front cover plate 62a. The front cover plate 62a is connected to the shield unit 42a via latch elements, which are not visible in detail. Preferably the front cover plate 62a comprises two opposite latching recesses, in each of which a respective latch element of the shield unit 42a engages. Due to the latching, the front cover plate 62a is easily demountable. This allows easy cleaning and/or simple exchange. The front cover plate 62a is embodied transparent. The front cover plate 62a is configured to protect the optical glare protection filter 10a. The front cover plate 62a covers the optical glare protection filter 10a from the outside.

Beyond this the glare protection device 12a comprises a head-fastening unit 64a. The head-fastening unit 64a is configured for fastening to a head of the user 38a. The head-fastening unit 64a is implemented by a head strap. The head-fastening unit 64a is invisibly connected to the shield unit 42a.

FIG. 7 shows the optical glare protection filter 10a during a darkening process at a point in time t. By way of the multiple contacting of the electrode layer units 18a, 18a', an advantageously high switching speed of the liquid-crystal cell 14a is achievable. Furthermore an advantageously homogeneous switching speed distribution of the liquid-crystal cell 14a is achievable. In contrast to an optical glare protection filter 10a that does not correspond to the invention, in which the electrode layer units are electrically contacted by only one contact element respectively, as shown in FIG. 8, by means of the optical glare protection filter 10a according to the invention a substantially more homogeneous switching speed distribution of the liquid-crystal cell 14a and a deeper darkening of the liquid-crystal cell 14a are achievable at the same point in time t of the darkening process. FIGS. 7 and 8 schematically show a state of the darkening of the liquid-crystal cell 14a, respectively of the liquid-crystal cell of the optical glare protection filter 66 that does not correspond to the invention, at a defined point in time t of the darkening process. Herein white areas represent portions of the liquid-crystal cell 14a in which an orientation of the crystal molecules of the liquid-crystal layer 16a is not yet fully accomplished. Light grey areas are herein portions of the liquid-crystal cell 14a in which a partial orientation of the crystal molecules of the liquid-crystal layer 16a is currently effected. Dark grey areas herein represent portions of the liquid-crystal cell 14a in which a complete orientation of the crystal molecules of the liquid-crystal layer 16a is already accomplished. Herein the transitions between the respective areas shown in the figures are represented discretely, for the sake of simplification. In a real application the transitions are principally gradual.

FIGS. 9 to 14 show four further exemplary embodiments of the invention. The following descriptions are substantially limited to the differences between the exemplary embodiments wherein, regarding structural components, features and functions that remain the same, the description of the other exemplary embodiments, in particular of FIGS. 1 to 8, may be referred to. For distinguishing the exemplary embodiments, the letter a in the reference numerals of the exemplary embodiment of FIGS. 1 to 8 has been substituted by the letters b to e in the reference numerals of FIGS. 9 to 14. Regarding structural components with the same designation, in particular regarding structural components with the same reference numerals, principally the drawings and/or the description of the other exemplary embodiments, in particular of FIGS. 1 to 8, may be referred to.

FIG. 9 shows an alternative optical glare protection filter 10b with a liquid-crystal cell 14b and with a contact unit 56b.

The optical glare protection filter 10b further comprises a first contact element 20b. The first contact element 20b is configured for electrically contacting a first electrode layer unit 18b. The optical glare protection filter 10b further comprises a second contact element 22b for electrically contacting the first electrode layer unit 18b. The second contact element 22b is substantially spaced apart from the first contact element 20b. A contacting point of the second contact element 22b for contacting the first electrode layer unit 18b is substantially spaced apart from a contacting point of the first contact element 20b for contacting the first electrode layer unit 18b. The second contact element 22b is arranged on a side of the first electrode layer unit 18b that is opposite the first contact element 20b. A partial zone of the first electrode layer unit 18b is arranged between the first contact element 20b and the second contact element 22b. The first contact element 20b and the second contact element 22b are arranged in opposite points of a total circumference of the first electrode layer unit 18b. The optical glare protection filter 10b moreover comprises five further contact elements 24b, 26b, 28b, 30b, 32b. The further contact elements 24b, 26b, 28b, 30b, 32b are also configured for electrically contacting the first electrode layer unit 18b. The further contact elements 24b, 26b, 28b, 30b, 32b are substantially spaced apart from the first contact element 20b and from the second contact element 22b as well as from one another. The contact elements 20b, 22b, 24b, 26b, 28b, 30b, 32b are respectively arranged on a circumference of the first electrode layer unit 18b. The contact elements 20b, 22b, 24b, 26b, 28b, 30b, 32b are successively arranged along the circumference. Contact elements 20b, 22b, 24b, 26b, 28b, 30b, 32b which are adjacent to one another along the circumference are respectively substantially spaced apart from each other. In the positions of the contact elements 20b, 22b, 24b, 26b, 28b, 30b, 32b the first electrode layer unit 18b extends through a sealing (not shown) of the liquid-crystal cell 14b to the outside, where the contact elements 20b, 22b, 24b, 26b, 28b, 30b, 32b contact the electrode layer unit with a flexprint. The contact elements 20b, 22b, 24b, 26b, 28b, 30b, 32b respectively implement a contacting of the first electrode layer 18b. For electrically contacting the first electrode layer unit 18b, the contact elements 20b, 22b, 24b, 26b, 28b, 30b, 32b are distributed substantially evenly in a circumferential direction around the first electrode layer unit 18b. The optical glare protection filter 10b moreover comprises a contact unit 56b. The contact unit 56b comprises the contact elements 20b, 22b, 24b, 26b, 28b, 30b, 32b. Beyond this the optical glare protection filter 10b comprises seven further contact elements 20b', 22b', 24b', 26b', 28b', 30b', 32b', which respectively electrically contact the second electrode layer unit 18b' of the liquid-crystal cell 14b. The second electrode layer unit 18b' is connected to the contact elements 20b', 22b', 24b', 26b', 28b', 30b', 32b' which correspond to the contact elements 20b, 22b, 24b, 26b, 28b, 30b, 32b which electrically contact the first electrode layer unit 18b. The contact elements 20b', 22b', 24b', 26b', 28b', 30b', 32b' electrically contacting the second electrode layer unit 18b' are also arranged substantially spaced apart from one another. The contact elements 20b', 22b', 24b', 26b', 28b', 30b', 32b' electrically contacting the second electrode layer unit 18b' have the same arrangement with respect to the second electrode layer unit 18b' as the contact elements 20b, 22b, 24b, 26b, 28b, 30b, 32b which electrically contact the first electrode layer unit 18b have with respect to the first electrode layer unit 18b. The contact unit 56b comprises the contact elements 20b', 22b', 24b', 26b', 28b', 30b', 32b' (FIGS. 9, 10).

The optical glare protection filter 10b further comprises a nose cut-out 36b,

FIG. 10 shows the optical glare protection filter 10b during a darkening process at a point in time t. Due to the multiple contacting of the electrode layer units 18b, 18b', it is possible to achieve an advantageously high switching speed of the liquid-crystal cell 14b. Moreover an advantageously homogeneous switching speed distribution of the liquid-crystal cell 14b is achievable. In contrast to an optical glare protection filter 66 that does not correspond to the invention, in which the electrode layer units are contacted with only one contact element 68 respectively (shown in FIG. 8), at the same point in time t of the darkening process a considerably more homogeneous switching speed distribution of the liquid-crystal cell 14b as well as deeper darkening of the liquid-crystal cell 14b are achievable by means of the optical glare protection filter 10b according to the invention. FIG. 10 schematically shows a state of the darkening of the liquid-crystal cell 14b at a defined point in time t of the darkening process.

FIGS. 12 to 14 respectively show alternative optical glare protection filters 10c, 10d, 10e with a liquid-crystal cell 14c, 14d, 14e and with a contact unit 56c, 56d, 56e. The optical glare protection filters 10c, 10d, 10e each have a rectangular basic shape. The optical glare protection filters 10c, 10d, 10e do not comprise a nose cut-out. FIGS. 12 to 14 show the optical glare protection filters 10c, 10d, 10e during a darkening process at a point in time t. Due to the multiple contacting of electrode layer units of the liquid-crystal cells 14c, 14d, 14e, it is possible to achieve an advantageously high switching speed of the liquid-crystal cell 14c, 14d, 14e. Moreover an advantageously homogeneous switching speed distribution of the liquid-crystal cell 14c, 14d, 14e is achievable. In contrast to an optical glare protection filter 66, which does not correspond to the invention, in which the electrode layer units are contacted with only one contact element 68 respectively (shown in FIG. 11), at the same point in time t of the darkening process a considerably more homogeneous switching speed distribution of the liquid-crystal cell 14c, 14d, 14e as well as a deeper darkening of the liquid-crystal cell 14c, 14d, 14e are achievable by means of the optical glare protection filters 10c, 10d, 10e according to the invention. FIGS. 12 to 14 schematically show a state of the darkening of the liquid-crystal cell 14c, 14d, 14e at a defined point in time t of the darkening process.

FIG. 12 shows an optical glare protection filter 10c with three contact elements 20c, 22c, 24c. The contact elements 20c, 22c, 24c are arranged side by side. The contact elements 20c, 22c, 24c are respectively arranged on a circumference of a first electrode layer unit. In the positions of the contact elements 20c, 22c, 24c the first electrode layer unit 18c extends through a sealing (not shown) of the liquid-crystal cell 14c to the outside, where the contact elements 20c, 22c, 24c contact the electrode layer unit 18c with a flexprint. The contact elements 20c, 22c, 24c respectively implement a contacting of the first electrode layer. A contact unit 56c comprises the contact elements 20c, 22c, 24c. Furthermore, the optical glare protection filter 10c comprises three further contact elements respectively electrically contacting the second electrode layer unit of the liquid-crystal cell 14c. The contact elements electrically contacting the second electrode layer unit have the same arrangement with respect to the second electrode layer unit as the contact elements 20c, 22c, 24c which electrically contact the first electrode layer unit have with respect to the first electrode layer unit.

FIG. 13 shows an optical glare protection filter 10d with six contact elements 20d, 22d, 24d, 26d, 28d, 30d. A second contact element 22d is arranged on a side of the first electrode layer unit that is opposite a first contact element 20d. The contact elements 20d, 22d, 24d, 26d, 28d, 30d are respectively arranged on a circumference of the first electrode layer unit. The contact elements 20d, 22d, 24d, 26d, 28d, 30d are arranged successively along the circumference. Contact elements 20d, 22d, 24d, 26d, 28d, 30d which are adjacent to each other along the circumference are respectively substantially spaced apart from one another. The contact elements 20d, 22d, 24d, 26d, 28d, 30d respectively implement a contacting of the first electrode layer. The contact unit 56d comprises the contact elements 20d, 22d, 24d, 26d, 28d, 30d. Moreover the optical glare protection filter 10d comprises six further contact elements, which respectively electrically contact the second electrode layer unit of the liquid-crystal cell 14d. The contact elements electrically contacting the second electrode layer unit have the same arrangement with respect to the second electrode layer unit as the contact elements 20d, 22d, 24d, 26d, 28d, 30d which electrically contact the first electrode layer unit have with respect to the first electrode layer unit.

FIG. 14 shows an optical glare protection filter 10e with eight contact elements 20e, 22e, 24e, 26e, 28e, 30e, 32e, 34e.

A second contact element 22e is arranged on a side of the first electrode layer unit that is opposite a first contact element 20e. The contact elements 20e, 22e, 24e, 26e, 28e, 30e, 32e, 34e are respectively arranged on a circumference of the first electrode layer unit. The contact elements 20e, 22e, 24e, 26e, 28e, 30e, 32e, 34e are arranged successively along the circumference. Contact elements 20e, 22e, 24e, 26e, 28e, 30e, 32e, 34e which are adjacent to each other along the circumference are respectively substantially spaced apart from one another. The contact elements 20e, 22e, 24e, 26e, 28e, 30e, 32e, 34e respectively implement a contacting of the first electrode layer. For an electrical contacting of the first electrode layer unit, the contact elements 20e, 22e, 24e, 26e, 28e, 30e, 32e, 34e are distributed substantially evenly around the first electrode layer unit in a circumferential direction. The contact unit 56e comprises the contact elements 20e, 22e, 24e, 26e, 28e, 30e, 32e, 34e, Moreover the optical glare protection filter 10e comprises eight further contact elements respectively electrically contacting the second electrode layer unit of the liquid-crystal cell 14e. The contact elements which electrically contact the second electrode layer unit have the same arrangement with respect to the second electrode layer unit as the contact elements 20e, 22e, 24e, 26e, 28e, 30e, 32e, 34e which electrically contact the first electrode layer unit have with respect to the first electrode layer. An arrangement and number of the contact elements 20e, 22e, 24e, 26e, 28e, 30e, 32e, 34e is herein to be understood just by way of example. Principally a different number and/or arrangement of the contact elements 20e, 22e, 24e, 26e, 28e, 30e, 32e, 34e, deemed expedient by someone skilled in the art, would also be conceivable.

The invention claimed is:

1. An optical glare protection filter for a glare protection device, comprising:
    at least one liquid-crystal cell further comprising at least one liquid-crystal layer and at least one first electrode layer configured to orient crystal molecules of the at least one liquid-crystal layer;
    at least one first contact element configured to electrically contact the at least one first electrode layer;
    at least one second contact element configured to electrically contact the at least one first electrode layer, the at least one second contact element being substantially spaced apart from the at least one first contact element; and
    at least one control and/or regulation unit configured to control and/or regulate a permeability of the optical glare protection filter depending on a captured operative state and/or on a light irradiation, wherein:
    the at least one control and/or regulation unit actuates the optical glare protection filter substantially simultaneously via the at least one first contact element and the at least one second contact element, and
    the at least one first contact element and the at least one second contact element darken homogeneously the at least one liquid-crystal cell.

2. The optical glare protection filter according to claim 1, wherein
    the at least one second contact element is arranged on a side of the at least one first electrode layer that is situated opposite the at least one first contact element.

3. The optical glare protection filter according to claim 1, comprising
    at least one further contact element configured to electrically contact the at least one first electrode layer, the at least one further contact element being substantially spaced apart from the at least one first contact element and the at least one second contact element.

4. The optical glare protection filter according to claim 1, wherein,
the at least one first contact element and the at least one second contact element are distributed substantially evenly in a circumferential direction around the at least one first electrode layer thereby electrically contacting the at least one first electrode layer.

5. The optical glare protection filter according to claim 1, further comprising
a nose cut-out, which is configured to at least partly accommodate a nose of a user.

6. The optical glare protection filter according to claim 1, comprising
at least two further contact elements, respectively electrically contacting at least one second electrode layer of the at least one liquid-crystal cell.

7. The glare protection device according to claim 1, further comprising
at least one shield unit, in which the optical glare protection filter is fixedly accommodated.

8. The optical glare protection filter according to claim 1, wherein
the liquid-crystal cell comprises at least one second electrode layer, which extends in parallel to the at least one first electrode layer,
the optical glare protection filter comprises at least two further contact elements respectively electrically contacting the at least one second electrode layer of the at least one liquid-crystal cell, wherein
the at least one second electrode layer is connected to the at least one first contact element and the at least one second contact element electrically contacting the at least one first electrode layer.

9. The optical glare protection filter according to claim 1, wherein
the at least one second contact element configured to electrically contact the at least one first electrode layer is spaced apart from the at least one first contact element by at least 1 cm.

10. The optical glare protection filter according to claim 1, wherein
the at least one second contact element configured to electrically contact the at least one first electrode layer is spaced apart from the at least one first contact element by at least 2 cm.

11. The optical glare protection filter according to claim 1, wherein
the at least one second contact element configured to electrically contact the at least one first electrode layer is spaced apart from the at least one first contact element by at least 3 cm.

* * * * *